(12) United States Patent
Jacobs et al.

(10) Patent No.: US 6,229,032 B1
(45) Date of Patent: May 8, 2001

(54) ELIMINATION OF TRANS-UNSATURATED FATTY ACID COMPOUNDS BY SELECTIVE ADSORPTION WITH ZEOLITES

(75) Inventors: Pierre A. Jacobs, Gooik; Pieter J. A. Maes, Harelbeke; Sabine J. Paulussen, Ravels; Mia Tielen, Linden; Danny F. E. Van Steenkiste, Zwijnaarde; Lieven K. Van Looveren, Merksplas, all of (BE)

(73) Assignee: K. U. Leuven Research & Development, Leuven (BE)

( * ) Notice: Subject to any disclaimer, the term of this patent is extended or adjusted under 35 U.S.C. 154(b) by 0 days.

(21) Appl. No.: 09/242,957

(22) PCT Filed: May 26, 1998

(86) PCT No.: PCT/EP98/03098

§ 371 Date: Sep. 21, 1999

§ 102(e) Date: Sep. 21, 1999

(87) PCT Pub. No.: WO98/54275

PCT Pub. Date: Dec. 3, 1998

(30) Foreign Application Priority Data

May 29, 1997 (EP) .................................................. 97108650

(51) Int. Cl.[7] ........................................................ C11B 3/10
(52) U.S. Cl. ............................................................. 554/191
(58) Field of Search ..................................... 554/191, 193

(56) References Cited

U.S. PATENT DOCUMENTS

| 4,048,205 | 9/1977 | Neuzil et al. . |
| 5,424,029 | 6/1995 | Kennedy et al. . |

FOREIGN PATENT DOCUMENTS 0233642   8/1987   (EP) .

OTHER PUBLICATIONS

"Oils–Fats–Lipids 1995," *Proc. World Congr. Int. Soc. Fat Res.*, 21st, vol. 1, 1996.

Brehm et al., "Verwendung von mit Platin beladenen Y–Zeolithen als Katalysatoren für die Hydrierung von flüssigen und niedrig schmelzenden Fetten," *Chemie. Ingenieur. Technik.*, vol. 61, No. 12, 1989, pp. 963–964.

Stashenko et al., "Catalytic transformation of Anise (pimpinella anisum L.) oil over zeolite Y", *J. High Resolution Chromatography*, vol. 18, No. 8, 1995, pp. 501–503.

Primary Examiner—Deborah D. Carr
(74) Attorney, Agent, or Firm—Banner & Witcoff, LTD.

(57) ABSTRACT

A novel process for the selective elimination of fatty acid compounds containing carbon-carbon double bonds in trans configuration from a substrate containing cis- and trans-isomers of said fatty acid compounds, by selective adsorption by a microporous zeolite material is disclosed. The pore size and shape of usable zeolite materials enable differentiation between cis- and trans-isomers of unsaturated fatty acid chains. The zeolite materials used have a selectivity ratio $\alpha_{trans/cis}$ higher than 1.00; this ratio is defined based on the elution properties of cis and trans double bond containing fatty acid methylesters dissolved in n-hexane during a column chromatography experiment with the zeolite material as the stationary phase and n-hexane as the mobile phase. Besides selective adsorption of trans-unsaturated fatty acid compounds, simultaneous or subsequent total or partial hydrogenation of the double bonds in said compounds can be carried out while using the same or similar zeolite material, containing finely dispersed catalytic active metals. The majority of these catalytic active sites must be inside the pores.

13 Claims, No Drawings

ELIMINATION OF TRANS-UNSATURATED FATTY ACID COMPOUNDS BY SELECTIVE ADSORPTION WITH ZEOLITES

This application is a 371 of PCT/EP 98/03098 filed May 26, 1998.

BACKGROUND OF THE INVENTION

The present invention relates to the selective elimination of trans-unsaturated double bonds in fatty acid compounds from a substrate containing cis- and trans-isomers of said fatty acid compounds. The elimination takes place by adsorption of said fatty acid compounds by zeolite materials having a selectivity towards trans-isomers. The invention also relates to the elimination of trans-isomers of said compounds by their selective adsorption by said zeolite materials further containing a metal catalyst, and saturation of the double bond of the fatty acid compounds adsorbed in the pores or cavities of said zeolite.

The aforementioned trans-unsaturated fatty acid compounds may be saponifiable or non saponifiable molecules. The saponifiable fatty acid compounds comprise esters, mono-, di- and triglycerides, phospholipids, glycolipids, diol esters of fatty acids, waxes and sterol esters. The non saponifiable compounds comprise free fatty acids, sterols, carotenoids, monoterpenes and tocopherols. Other fatty acid compounds well known for their amphiphilic properties are fatty acid derivatives like fatty alcohols, fatty amines or fatty acid dimers. The present invention relates, in particular, to the elimination of trans-unsaturated fatty acid residues in triglycerides from edible oils and fats and is therefore mostly related to food technology.

Oils and fats for food applications are mainly triglycerides: molecules having three fatty acids esterified with glycerol. In most cases, the fatty acid chains are not branched, have a chain length of 4 to 24 carbon atoms, and may contain up to three double bonds. The physicochemical properties of triglycerides strongly depend on the chemical structure of the fatty acid residues and more particularly on their chain length and the amount of double bonds present. In fact, the melting point of triglycerides increases with increasing chain length and decreasing unsaturation of the fatty acid residues present.

Hardening by hydrogenation is a common process to increase the melting profile of edible oils and fats. In most cases, this process is carried out as a heterogeneous reaction with hydrogen gas and a heterogeneous catalyst. Often used catalyst materials are metals like nickel or palladium finely deposited on carriers like kieselguhr or silica. The hydrogenation process is typically carried out in agitated batch autoclaves at temperatures above 400 K and hydrogen gas pressures above 0.1 MPa. Agitation can be realised by stirring or by more complex systems like circulating the reactors content through a venturi system where hydrogen is mixed intensively with the oil being hydrogenated. Continuous processes are used as well.

Hydrogenation can be carried out to accomplish complete saturation of all double bonds present. In many cases, however, partial hydrogenation is aimed for. In the latter case and with the processes actually used industrially, isomerisation of carbon-carbon double bonds in the fatty acid residues occurs besides the saturation of double bonds by the addition of hydrogen. For food applications, starting materials for hydrogenation are of biological origin. In such materials, like palm oil, soybean oil, softseed oils and the like, almost no trans-isomers are present; the position of the double bonds in the fatty acid chains is well defined too. Hydrogenation by means of metal catalysts like nickel, palladium, platinum, ruthenium, rhodium and others, inevitably leads to cis/trans-isomerisation, since the reaction mechanism using such catalysts implies a transition state with a freely rotating semi-hydrogenated configuration (L. F. Albright, *J. Am. Oil Chem. Soc.*, 40/5, 16 (1963) and G. Cecchi, G. Mallet, E. Ucciani, *Riv. Ital. Sost. Grasse*, 58/5, 228 (1981) and R. R. Allen, *J. Am. Oil Chem. Soc.*, 63/10, 1328 (1986)). The existence of this transition state also leads to positional isomerisation of double bonds when the total addition of hydrogen is sufficiently slow. Just like saturated fatty acids, such isomeric fatty acid residues increase also to some extent the melting profile of triglycerides.

Although hydrogenation is the main cause for the presence of fatty acid isomers in food oils and fats, similar isomers can be found in other lipids too. Animal fats like butter fat or tallow have some trans-isomers, and fully refined, non-hydrogenated fats also may contain a very low content of said isomers due to the high temperature processing on refining and deodorisation (L. H. Wesdorp, *Lipid Techn.*, 8/6, 129 (1996)). However, the amount of isomers present in all these is significantly lower than one can expect in general in hardened products.

According to recent studies, a lot of controversy has been risen about possible health hazards of these trans-unsaturated fatty acids (M. B. Katan, P. L. Zock, R. P. Mensink, *Annu. Rev. Nutr.*, 15, 473, (1995) and British Nutrition Foundation, "Trans Fatty Acids", (1995)).

For that reason, attempts have been made to reduce the trans fatty acid content in food products. An important contribution is the reduction of these trans fatty acids in hydrogenated edible fats (J. M. Hasman, *Inform*, 6/11, 1206 (1995)). A lot of hydrogenation process modifications have been proposed to achieve this objective.

The hydrogenation process of vegetable oils is generally carried out in an agitated batch autoclave. Typical process parameters are a hydrogen pressure ranging from 0.1 to 0.5 MPa and a hydrogenation temperature ranging from 400 to 475 K. Since isomerisation depends on the concentration and lifetime of the so-called semi-hydrogenated transition state, a first approach to reduce isomerisation relies on increasing the hydrogen concentration on the catalyst active sites. This can typically be realised by a higher pressure of hydrogen gas supplied, to increase its solubility in the oil, and by increasing the hydrogen mass transfer coefficient, by more efficient agitation (P. R. Puri, *J. Am. Oil Chem. Soc.*, 55/12, 865 (1978) and J. W. E. Coenen, *Riv. Ital Sost. Grasse*, 58/9, 445 (1981)). Similarly, a reduction of the reaction temperature has been proven to have some effect on the isomerisation of double bonds, more specifically a suppression of trans double bond formation, but also brings along a reduced reaction velocity. Both means, increase of hydrogen concentration and temperature lowering, although effective to some extent in lowering the concentration of isomerised products in hardened oils and fats, can not eliminate isomers, mainly transisomers, in said oils and fats.

A second approach one has followed to reduce trans-unsaturated fatty acid compounds is to influence the catalytic system itself The metal particles commonly used are as small as 20–50 Å in order to provide a high reaction surface area. To modify the catalytic properties of the metallic catalyst, alloying (P. N. Rylander, *J. Am. Oil Chem. Soc.*, 47, 482 (1970) and A. I. Thomson, *J. Chem. Tech. Biotech.*, 37, 257 (1987) and J. D. Parry, *J. Chem. Tech. Biotech*, 50, 81 (1991)) or addition of modifiers like amine or ammonium compounds (U.S. Pat. No. 4,307,026 and U.S. Pat. No. 4,228,088 and EP-A-0,576,477 and E. Draguez de Hault, *J. Am. Oil Chem. Soc.*, 65, 195, (1984)) have been used to decrease the isomerisation effects like trans double bond formation.

Still other means have been used to influence the concentration of trans-unsaturated fatty acid compounds. Homogeneous catalysis with metal complexes like benzoate-Cr(CO)$_3$ or triphenylphosphine complexes of ruthenium or rhodium has been investigated on small scale (E. N. Frankel, *J. Am. Chem. Soc.*, 90, 2446, (1968) and C. Bello, *Ibid.*, 62, 1587, (1985) and E. A. Emken, *J. Am. Oil Chem. Soc.*, 65, 373, (1988)). A reduction of the trans fatty acid formation upon hydrogenation was realised. Industrial use, however, can not be expected since the catalysts used, could be toxic and could not be removed easily and economically after hydrogenation. Attempts to heterogenise the catalytic systems mentioned were not successful Besides changing of the hydrogenation process parameters, use of modifiers, alteration of the catalytic metal function and specific supporting of the metal to decrease the trans-isomeric fatty acid content upon hydrogenation, has been studied. Supporting the metal on different materials like titaniumdioxide and kieselguhr has been published (E. Draguez de Hault, *J. Am. Oil Chem. Soc.*, 65, 195 (1984). A high dispersion of the metal in a porous structure has been accomplished according to EP-A-0,233,642, U.S. Pat. No. 4,584,139 and U.S. Pat. No. 5,492,877. However, none of these could eliminate trans-unsaturated fatty compounds from the substrates studied completely.

Still further attempts have been carried out to influence the cis/trans-isomerisation during hydrogenation. Electrocatalytic hydrogenation by the addition of hydrogen donors, although decreasing isomerisation, still produced trans-isomers; in addition, the velocity of the reaction was lower (EP-A-0,429,995 and U.S. Pat. No. 4,399,007 and G. J. Yusem, *J. Am. Oil Chem. Soc.*).

Hydrogenation of fats and oils on zeolites has been reported by Koritala (S. Koritala, *J. Am. Oil Chem. Soc.*, 45, 197, (1968)). Pt/Na—Y zeolite was found to be able to hydrogenate triglyceride samples; cis/trans-isomerisation, however, could not be eliminated (A. Brehm and H. M. Polka, *Chem.-Ing. Tech.*, 61, 963, (1989)). Pd/CuO/ZnO/ZSM-5 has been used to hydrogenate methyllinoleate, although with low conversion, without any trans-isomer formation; this catalyst wasn't very active for the hydrogenation of triglycerides (R. Müller, "Selektieve Hydrierung von Ölen an suspendierten Katalysatoren", MSc thesis, Oldenburg, (1991)). The authors report on the introduction of a hydrogenation selectivity for a palladium loaded zeolite material by having copperoxide and zincoxide inside the pores as well. During the preparation of said metal loaded zeolite material, after the oxidation step, a subsequent reduction below 473 K is required to have a catalytically active palladium while the oxides of copper and zinc, which are required to obtain the selectivity, survive this reductive operation. The elimination of trans isomers with this metal alloy loaded catalyst, however, can not be attributed to selective adsorption of said trans fatty acid isomers, but by excluding formation of trans-unsaturated fatty acid compounds. The effect, also according to the authors, must be the result of the restricted mobility of the semi-hydrogenated transition state when present in the pores of the zeolite material. To increase activity, they recommend to widen the pores of the zeolites. This, however, will certainly not increase the selectivity for the adsorption of trans fatty acid compounds.

It should be clear that the above mentioned methods to avoid isomerisation, mainly cis/trans-isomerisation, are just partial solutions for what one should aim for: a substrate without any residual trans-unsaturated fatty acid compounds left. The present invention will overcome all drawbacks of the prior art in providing a process for the adsorption of transunsaturated fatty acid compounds from substrates containing cis- and trans-isomers of said compounds by a microporous zeolite material having a selectivity for the adsorption of said trans-unsaturated compounds bigger than one.

OBJECT OF THE INVENTION

It is the object of the present invention to provide a process that allows the complete elimination of trans unsaturated fatty acid compounds from a substrate containing cis and trans isomers of said fatty acid compounds by means of a microporous zeolite material having a selectivity $\alpha_{trans/cis}$ higher than one. This and other objects and advantages of the present invention will become apparent as the description of the invention proceeds.

DETAILED DESCRIPTION OF THE INVENTION

According to the present invention a process is provided to eliminate trans-unsaturated fatty acid compounds from a substrate containing cis- and trans-isomers of said fatty acid compounds, in which process the trans-unsaturated fatty acid compounds are selectively adsorbed by a microporous zeolite material.

In general zeolites are crystalline aluminosilicates in which the three components aluminium, silicon and oxygen are arranged in a fixed, dimensional framework with cavities and pores of uniform size and shape. The zeolite network is composed of SiO$_4$ and AlO$_4$ tetrahedra in which the negative charge on the latter is neutralised by cations like metal ions, ammonium ions or alkali metal ions.

A general formula for an aluminosilicate based zeolite can be written as:

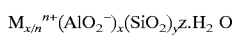

$$M_{x/n}{}^{n+}(AlO_2{}^-)_x(SiO_2)_y \cdot z \cdot H_2O$$

where n is the valence of the charge compensating cation M and the x/y ratio is smaller than or equal to one according to the Loewenstein rule (D. W. Breck, "Zeolite Molecular Sieves", J. Wiley and Sons, 1974).

Zeolites can be synthesised with different topologies giving rise to pores with different size, shape and dimensionality. The aperture sizes of these micropores generally ranges between 0.4 and 0.8 nm, depending on the number of tetrahedra in the ring that member them. The dimensions of the pore apertures manage the accessibility of the internal volume of the zeolite by excluding molecules with dimensions exceeding those of the aperture of the zeolite pores. Zeolites with a three-dimensional network of pores are particularly interesting in this invention for obtaining a large accessibility of the substrate molecules and a high potential metal dispersion (P. B. Weisz and V. J. Frilette, *J. Phys. Chem.*, 64, 342 (1960)).

Three different molecular shape selective effects are known in zeolite literature. The first, reactant shape selectivity, appears in the selectivity of the aperture of the zeolite pore in admitting preferentially one molecule with a typical size or shape out of a mixture of molecules. The selective hydrogenation of unbranched α-olefins out of a mixture containing branched analogues on Pt/ZSM-5 is well known in the art (P. B. Weisz, *Chemtech*, 3, 498, (1973) and R. M. Dessau, *J. Catal.*, 89, 520, (1984)). The selective hydrogenation of trans-2-butene out of a cis/trans-mixture on Pt/A is known in literature (N. Y. Chen, P. B. Weisz, *Chem. Eng. Prog Symp. Ser.*, 73, 86, (1967)).

A second type of selectivity is defined as product shape selectivity: the product of a reaction catalysed by zeolites must have a specific size or configuration to have the possibility to migrate out of the pores and cages of the zeolite material used. As an example, product selectivity has been shown by the absence of branched products like isobutane and isopentane in the cracking of n-alkanes on 8-membered ring zeolites.

The third type of selectivity is the transition state shape selectivity. The zeolite pore size and shape control the permissible size and shape of the transition state between reactant and product molecules. An example is the cracking of n-hexane out of a mixture of n-hexane and 3-methylpentane on H-ZSM-5 (N. Y. Chen, W. E. Garwood, *J. Catal.*, 52, 453, (1978)).

We have extensively studied and selected, out of a large number of different zeolite materials, those that permit the linear trans-unsaturated fatty acid chains of fatty acid compounds to enter inside the zeolite pores while simultaneously limiting or excluding the access of those pores by the bended cis-unsaturated fatty acid chains of said compounds. Typical zeolite materials having this selectivity are microporous and have a 10-membered ring structure. They preferably have a high $Si/Me^{3+}$-ratio of their chemical composition, even more preferable higher than 39 and most preferable higher than 77.5. A typical example is a ZSM-5 zeolite. The $Me^{3+}$ in many cases is alumina, but other trivalent kations like boron or iron are possible candidates as well. In general $Me^{3+}$ represents all trivalent kations be it alumina, others or mixtures thereof. A zeolite material having an extremely high $Si/Me^{3+}$ratio and having the required properties as described in the invention is silicalite.

The selectivity meant in this description of the invention can be defined based on a simple but well defined liquid chromatographic method. To determine the selectivity of the zeolite structures studied, a model solution of methyloleate and methylelaidate has been introduced. The chromatographic response curves are analysed according to the method of moments (D. M. Ruthven, "Principles of Adsorption and Adsorption Processes", J. Wiley and sons, (1984)) wherein the first moment is related to the adsorption equilibrium constant of the methylester. The voidage of the adsorbent column was calculated based on the fractional micropore volume of the zeolite crystals (D. W. Breck, "Zeolite Molecular Sieves", J. Wiley and sons, (1974)). For a packed column of zeolite adsorbent the first moment of the response curve is denoted as:

$$\mu \equiv \frac{\int_0^\infty c*t*dt}{\int_0^\infty c*dt} = \frac{L}{\varepsilon*v} * [\varepsilon + (1-\varepsilon)*K]$$

wherein $\mu$ is the mean of the response curve (s), c the concentration of methyloleate and methylelaidate respectively in the fluid phase (moles/cm³), t the time (s), L the length of the adsorbent column (cm), $\varepsilon$ the voidage of the adsorbent bed, v the interstitial liquid velocity (cm/s) and K the adsorption equilibrium constant [(moles/cm³ crystal)/(moles/cm³ solution)]. $\alpha$ is the separation factor (D. D. Do, P. L. J. Mayfield, *American Institute of Chemical Engineers Journal*, 33, 1397 (1987)) or the selectivity ratio between methylelaidate and methyloleate and is hereby denoted as:

$$\alpha_{trans/cis} = \frac{K_{trans}}{K_{cis}}$$

On studying different zeolites, surprisingly we found those zeolites having a selectivity ratio $\alpha_{trans/cis}$, as defined and determined by the described method, being higher than one, to adsorb selectively trans-unsaturated fatty acid compounds out of a substrate containing cis- and trans- isomers of said compounds. Zeolites having a selectivity ratio $\alpha_{trans/cis}$ higher than 1.10 have been found to be even more performant to selectively adsorb trans-unsaturated fatty compounds out of a substrate containing cis- and trans-isomers of said compounds.

The concentration of trans-unsaturated fatty acid compounds in the substrate and the ratio of cis- and trans-isomers in it can differ widely. For substrates with a low concentration of trans-unsaturated fatty acid compounds, a specific way to carry out the process described in the present invention, is by simple adsorption and subsequent removal of the microporous zeolite adsorbent loaded with the trans-unsaturated fatty acid compounds, leaving a mixture exempt of said compounds. Purification of fully refined edible oils that contains some triglycerides with trans double bonds due to a high temperature desodorisation treatment, can be carried out according to this specific adsorption process. Soybean oil, rapeseed oil, palm oil and others are suitable substrates, but other oils from vegetable or animal origin can be treated similarly. The adsorption process can be carried out batchwise or continuously by using a column reactor filled with the appropriate zeolite adsorbent.

For substrates having high levels of trans-unsaturated fatty acid compounds, the just explained process variant to eliminate said compounds is not attractive because of low yield and high costs.

By depositing inside the pores of such zeolite materials, metals like nickel, platinum, palladium, ruthenium, rhodium, cobalt, copper or mixtures thereof and having catalytic activity for the hydrogenation of carbon-carbon double bonds, we further surprisingly found to have means to produce hydrogenated fatty acid containing compounds without transisomers. To achieve the latter a two step hydrogenation process can be used. In that case, fatty acid containing compounds hydrogenated by methods described in the state of the art and thus undoubtedly containing trans-unsaturated fatty acid compounds, are treated consecutively or simultaneously with zeolites according to the present invention. Complete elimination of trans-isomers in hardened products is thus obtained.

Substrates to be used for the process described in the present invention can be mixtures of cis- and trans-unsaturated fatty acid compounds with or without solvents. When solvents are used, a higher adsorption rate is reached by lowering the viscosity of the substrate comprising the trans fatty acid containing compounds. Fatty acid containing compounds can be methylesters as used in the method to determine the selectivity ratio of zeolite materials for the adsorption of trans-unsaturated fatty acid compounds. Other compounds are used for food applications like triglycerides present in edible oils and fats be it partially hydrogenated or not, and di- or monoglycerides used as emulsifiers. Still other substrates containing trans- unsaturated fatty acid compounds for similar or other applications can also be treated according to the present invention. Said compounds can be sugar esters of fatty acids, polyol fatty acid esters, fatty alcohols, fatty amines, dimeric fatty acids, waxes and others being derivatives of fatty acids.

The microporous zeolite with the required adsorptive properties can be regenerated after use in adsorption by leaching with solvent or other methods like incineration in specific processes. Said zeolites also containing catalytic metals and therefor used for the production of hydrogenated products containing no trans-unsaturated fatty acids compounds, could be reused as such, or if necessary after reactivating by appropriate methods like decoking and reduction.

The invention will now be described further by the following section on materials and methods and illustrative but non-limiting examples.

Materials and Methods

Zeolite Y (PY-43) is obtained from Uetikon (CU Chemie Uetikon AG, CH-8707 Uetikon) and ZSM-5 (CBV-8020 and CBV-1502) is supplied by PQ (1700 Kansas Avenue, Kans. 66105-1198). ZSM-22 and ZK-5 are synthesised according to published procedures (P. A. Jacobs, J. A. Martens, *Stud Surf. Sci. Catal,* 33, Elsevier, (1987) and W. M. Meier, G. T. Kokotailo, *Z. Kristallogr.,* 121, 211, (1965)). Calcined zeolite Y and ZSM-5 are twice ion exchanged overnight with a 1.0 M aqueous solution of NaCl, typically 300 ml solution for 1 g of catalyst to accomplish a complete sodium form of the zeolite. The Na-zeolite thus obtained is centrifuged, washed till Cl-free upon addition of a 0.01 N solution of $AgNO_3$ to the filtrate and dried at 393 K during 3 to 4 hours until constant weight. Pt-zeolite is prepared by ion exchange with $Pt(NH_3)_4Cl_2$. The ion exchange is carried out with 1025.2 ml of a $1.10^{-4}$ M solution of $Pt(NH_3)_4Cl_2$ for 2 g of Na-zeolite. The Pt-zeolite thus obtained is filtered, washed till Cl-free and dried at room temperature. Calcination of the catalyst is performed by heating at about 0.5 K/min to 623 K for at least one hour under a flow of oxygen, hereby decomposing the Pt-amine complex. After cooling down the sample, the Pt(II) is reduced to the metal state by heating at 0.5 K/min to 773 K for one hour under a flow of hydrogen. The acid sites inherently formed by reducing the Pt(II) to the metal state are neutralised under a flow of ammonia at 473 K for at least one hour. The hereby formed ammonium ions are exchanged with sodium according to the aforementioned method. The obtained zeolite catalyst contains 1 wt. % of platinum.

A second series of samples is prepared. Calcined zeolite ZK-5 and ZSM-5 are ion exchanged with a 0.1 M aqueous solution of NH4Cl, typically 100 ml solution for 1 g of catalyst, under reflux for 4 hours. The hereby obtained $NH_4$-zeolite is filtered, washed till Cl-free and calcined at 1 K/min to 673 K for a least one hour to remove the ammonia from the catalyst medium. The acid form of the zeolite powder is mixed with calculated amounts of $PtCl_2$, typically 13.63 mg of $PtCl_2$ to 1 g of catalyst, under inert atmosphere to avoid hydrolysis of the metal chloride and hydration of the zeolite. The solid mixture is heated at 5 K/min to 823 K under nitrogen atmosphere to perform solid state ion exchange. Hydrogen chloride is formed in situ and purged out of the reactant medium. After cooling down the sample to room temperature, the Pt(II) is reduced to its metal state by heating at 0.5 K/min to 673 K for one hour under a flow of hydrogen. The acid sites are neutralised by a flow of ammonia and ammonium ions formed are exchanged with sodium according to the aforementioned method. The obtained zeolite sample contains 1 wt. % of platinum.

The adsorption experiments of methyloleate and methylelaidate are performed by liquid phase chromatography (HPLC) on a packed bed of zeolite crystals. The metal column (4.6 mm internal diameter and 48 mm packed length) contains the zeolite adsorbent enclosed by two 0.5 μm filters (Alltech, Deerfield, Ill. USA). A liquid chromatography metering pump (HP1090, Hewlett Packard, Waldbronn, Del.) provides a steady flow of n-hexane through the adsorbent column of packed zeolite crystals. The eluent is monitored by a refractive index detector (R. I. HP1047A, Hewlett Packard, Waldbronn, Del.). A small column filled with molecular sieve pellets (5A, E. Merck, Darmstadt, Del.) is placed in line between the outlet of the pump and the chromatographic column to dry the mobile phase (n-hexane) continuously, since water could influence the adsorption equilibrium constants. The mobile phase is continuously dried over a packed column of molecular sieve pellets (5A, E. Merck, Darmstadt, Del.) to avoid interaction of water on the adsorption equilibrium constant. A small pulse (20 μl) of pure (99 wt. %) and methylelaidate (99 wt. %) (both: Fluka Chemie AG, Buchs, CH) is injected separately at time zero and the concentration response at the outlet of the column is monitored on the R. I. detector. The adsorption measurements are performed at 338 K. Systems linearity is confirmed by replicate experiments in which the flow rate of n-hexane is varied between 1 ml/min and 4 ml/min. Zeolites ZK-5, ZSM-5, ZSM-22, Y, Mordenite (CBV 30A, PQ, Kans., USA) and Beta (PB-1, Chemie Uetikon AG, Uetikon, CH) are ion exchanged with an aqueous solution of NaCl according to the prescribed method. The resulting Na-zeolite is calcined at 2 K/min to 373 K for 1 hour and consequently at 2 K/min to 773 K for at least 2 hours. The packed bed of Na-zeolite is calcined at about 1 K/min to 623 K for at least 6 hours under a flow of high pressure nitrogen.

The selectivity ratio $\alpha_{trans/cis}$ is determined by interpretation of the chromatographic response curves according to the method of moments (D. M. Ruthven, "Principles of Adsorption and Adsorption Processes", J. Wiley and sons (1984)). A detailed description of the calculation method has been described before in the detailed description of this invention.

The selective hydrogenation of trans-unsaturated fatty acid compounds from a mixture containing both cis- and trans-isomers is carried out in a batch reactor. 8 ml of an octane solution of cis- and trans-unsaturated fatty acids or methylesters is loaded in a 10 ml reactor (home made, KULeuven, BE) and the catalyst, prepared as described above, is added. The reactor is closed, purged with nitrogen and heated. A hydrogen pressure of 6 MPa is applied while stirring the mixture at approximately 500 rpm. The hydrogenation reaction is performed at 338 K. A sample of 0.25 ml is withdrawn from the reactor after 15, 30 and finally after 60 min respectively and centrifuged to remove the catalyst. The samples are analysed by isothermal gas chromatography at 353 K on a BPX-70 column (SGE, Austin, USA). When needed, samples are derivatised to enable analytical differentiation between cis- and trans-isomers. Triacylglycerols are transesterified to methylesters of their fatty acid chains. To 0.25 ml of the triglyceride sample 1 ml diethylether and 1 ml of a 3 wt. % solution of potassium hydroxide in anhydrous methanol is added. The mixture is shaken vigorously and after 3 minutes the transesterification is stopped by adding 1 ml of distilled water. Fatty acid methylesters are then extracted with n-pentane. The organic layer is washed several times with water and finally dried over molecular sieve (5A, E. Merck, Darmstadt, Del.). Relative sensitivity coefficients of methyloleate, methylelaidate, methylstearate and methylpalmitate are determined with methyldecanoate as standard. The disappearance, i.e. conversion of cis- and trans-unsaturated methylesters to saturated ones and denoted as $X_{cis}$, (%) and $X_{trans}$ (%) respectively is determined after 60 min reaction time. The first order reaction rate constants of cis- and trans-unsaturated methylesters denoted as $k_{cis}$ and $k_{trans}$ in $h^{-1}$ respectively are determined after 15 min.

A rapeseed oil is partially hydrogenated with 0.2 wt. % of a supported Ni-catalyst (21 wt. % Ni on silica, Pricat 9910, Unichema, Emmerich, Del.) at 423 K and 0.3 MPa during 150 min in an agitated autoclave.

EXAMPLES

Examples 1 to 4

Na-ZK-5, Na-ZSM-5 and Na-ZSM-22 crystals are packed in an adsorbent bed and calcined according to the prescribed methods. The separation factor $\alpha_{trans/cis}$ for these zeolites is higher than 1 and corresponds to the present invention. The results of the adsorption measurements, represented in the adsorption equilibrium constants of methyloleate and methylelaidate and the separation factor $\alpha_{trans/cis}$ are presented in table 1.

TABLE 1

| Example No. | 1 | 2 | 3 | 4 |
|---|---|---|---|---|
| Catalyst | Na-ZK-5 | Na-ZSM-5 | Na-ZSM-5 | Na-ZSM-22 |
| Si/Al | 2.3 | 39 | 77.5 | 45 |
| crystal size (μm) | n.d.* | 0.3–0.6 | 0.5–2 | n.d. |
| Adsorption | | | | |
| $K_{trans}$ | 0.91 | 3.23 | 6.09 | 2.34 |
| $K_{cis}$ | 0.88 | 3.08 | 5.08 | 2.21 |
| $\alpha_{trans/cis}$ | 1.03 | 1.05 | 1.21 | 1.05 |

*not determined

Comparative Example 5 to 7

Na-Y, Na-Mordenite and Na-Beta are pretreated according to prescribed methods. The separation factor $\alpha_{trans/cis}$ for these zeolites as demonstrated in table 2 is lower than 1.

TABLE 2

| Example No. | 5 | 6 | 7 |
|---|---|---|---|
| Catalyst | Na-Y | Na-Mordenite | Na-Beta |
| Si/Al | 2.7 | 17.5 | 9.9 |
| crystal size (μm) | 2–3 | n.d. | 0.2–0.4 |
| Adsorption | | | |
| $K_{trans}$ | 8.77 | 0.98 | 25.94 |
| $K_{cis}$ | 9.73 | 1.03 | 29.23 |
| $\alpha_{trans/cis}$ | 0.90 | 0.96 | 0.89 |

Comparative Examples 8 to 11

The following examples illustrate the catalytic hydrogenation activity and selectivity of Pt/Na-ZK-5, Pt/Na-ZSM-5, Pt/Na-ZSM-22 and Pt/Na—Y as prepared according to prescribed methods. The catalytic hydrogenation conditions as well as the analytical methods for sample analysis are represented before. A solution of methyloleate and methylelaidate is applied as lipid source. The catalyst and substrate composition and the reaction results are given in table 3. The first order reaction rate constants of methyloleate and methylelaidate are determined after 1 hour.

TABLE 3

| Example No. | 8 | 9 | 10 | 11 |
|---|---|---|---|---|
| Catalyst | Pt/Na-ZK-5 | Pt/Na-ZSM-5 | Pt/Na-ZSM-22 | Pt/Na-Y |
| topology | KFI | MFI | TON | FAU |
| Si/Al | 2.3 | 77.5 | 45 | 2.7 |
| Pt/lipid (mg/g) | 1.42 | 1.29 | 1.87 | 1.32 |
| Lipid (wt.%) | | | | |
| methyloleate | 4.17 | 3.99 | 3.86 | 4.20 |
| methylelaidate | 2.71 | 2.76 | 2.77 | 2.91 |
| Hydrogenation | | | | |
| $k_{cis}$ ($h^{-1}$) | 0.032 | 0.278 | 0.223 | 5.537 |
| $k_{trans}$ ($h^{-1}$) | 0.022 | 0.197 | 0.149 | 1.135 |
| $k_{trans}/k_{cis}$ | 0.66 | 0.71 | 0.67 | 0.20 |
| $X_{cis}$ (%) | 2.4 | 33.8 | 9.3 | 95.6 |
| $X_{trans}$ (%) | 1.8 | 25.3 | 5.6 | 68.1 |

These examples confirm the influence of the pore size and topology of the zeolite on the hydrogenation activity and selectivity promoting the Pt/Na-ZSM-5 (MFI) as an optimal zeolite structure. Since no selectivity towards methylelaidate is noticed, a further optimisation of the catalyst design is required.

Examples 12 to 14

Following examples illustrate the effect of a finely dispersed metal catalyst in the zeolite pores on the hydrogenation selectivity of methylelaidate. Pt/Na-ZSM-5 is prepared by competitive ion exchange of $Pt(NH_3)_4Cl_2$ and NaCl with a Na/Pt molar ratio of 25. The obtained zeolite is washed and calcined according to prescribed methods. The zeolite samples are oxidised at two different temperatures, 773 K (examples 10 and 11) and 623 K (example 12) respectively. The reaction conversions and the rate constants are given in table 4. The effect of conditions for preparation of said zeolites is clearly illustrated.

TABLE 4

| Example No. | 12 | 13 | 14 |
|---|---|---|---|
| Catalyst | Pt/Na-ZSM-5 | Pt/Na-ZSM-5 | Pt/Na-ZSM-5 |
| Si/Al | 39 | 77.5 | 77.5 |
| oxidation T (K) | 773 | 773 | 623 |
| Pt/lipid (mg/g) | 8.01 | 8.30 | 5.44 |
| Lipid (wt.%) | | | |
| methyloleate | 0.56 | 0.52 | 0.84 |
| methylelaidate | 0.55 | 0.57 | 0.79 |
| Hydrogenation | | | |
| $k_{cis}$ ($h^{-1}$) | 0.247 | 0.285 | 0.093 |
| $k_{trans}$ ($h^{-1}$) | 0.298 | 0.892 | 0.523 |
| $k_{trans}/k_{cis}$ | 1.20 | 3.13 | 6.25 |
| $X_{cis}$ (%) | 11.7 | 20.4 | 9.9 |
| $X_{trans}$ (%) | 17.9 | 39.9 | 18.9 |

Example 5

In the following example a partially hydrogenated rapeseed oil is hydrogenated on a Pt/Na-ZSM-5 zeolite as prepared according to the prescribed method in example 13. Only the mono-unsaturated compounds are taken into account for the rate constants and the conversions of the cis- and trans-unsaturated fatty acids are illustrated in table 5.

TABLE 5

| Example No. | 15 |
| --- | --- |
| Catalyst | Pt/Na-ZSM-5 |
| Si/Al | 77.5 |
| Pt/lipid (mg/g) | 9.80 |
| Fatty acid composition* (wt.%) | |
| saturated | 17.47 |
| mono-unsaturated (cis) | 31.23 |
| mono-unsaturated (trans) | 49.37 |
| di-unsaturated | 1.93 |
| Hydrogenation | |
| $k_{cis}$** (h$^{-1}$) | −0.081 |
| $k_{trans}$ (h$^{-1}$) | 0.371 |
| $X_{cis}$ (%) | 0.47 |
| $X_{trans}$ (%) | 15.4 |

*The lipid concentration is 1.79 wt. % and the fatty acid composition is determined by methanolysis according to the prescribed method. The saturated compounds can be subdivided in laurate (0.08 wt. %), myristate (0.12 wt. %), palmitate (6.44 wt. %), stearate (9.78 wt. %), arachidate (0.66 wt. %) and behenate (0.37 wt. %). The mono-unsaturated compounds are mainly composed of oleate (cis9, 14.51 wt. %) and elaidate (trans9, 27.26 wt. %) and positional isomers thereof
**Initial formation of cis-unsaturated fatty acids occur

What is claimed is:

1. Process for the elimination of trans-unsaturated fatty acid compounds from a substrate containing cis- and trans-isomers of said fatty acid compounds, wherein the trans-unsaturated fatty acid compounds are selectively adsorbed by a microporous zeolite material having a selectivity ratio $\alpha_{trans/cis}$ higher than 1.

2. Process according to claim 1, wherein the microporous zeolite material has a selectivity ratio $\alpha_{trans/cis}$ higher than 1.10.

3. Process according to claim 1, wherein the microporous zeolite material has a 10-membered ring pore structure and a Si/Me-ratio higher than 39, preferably higher than 77.5.

4. Process according to claim 1, wherein the fatty acid compounds are selected from the group consisting of free fatty acids, monoglycerides, diglycerides, triglycerides, phospholipids, glycolipids and mixtures thereof.

5. Process according to claim 4, wherein the fatty acid compounds are triglycerides.

6. Process according to claim 1, wherein subsequent to the selective adsorption of trans-unsaturated fatty acid compounds, the microporous zeolite material is removed from the substrate.

7. Process according to claim 1, wherein the selective adsorption of the trans-unsaturated fatty acid compounds is carried out with a continuous substrate supply on a packed bed of microporous zeolite material.

8. Process according to claim 1, wherein the microporous zeolite material comprises, inside its pores, a hydrogenation metal catalyst selected from the group consisting of platinum, palladium, nickel, copper, cobalt, rhodium, ruthenium and mixtures thereof.

9. Process according to claim 8, wherein the hydrogenation metal catalyst is nickel.

10. Process according to claim 8, wherein the microporous zeolite material catalyses the saturation of the trans carbon-carbon double bonds of the trans-unsaturated fatty acid compounds selectively adsorbed by the microporous zeolite material.

11. Process according to claim 2, wherein the microporous zeolite material has a 10-membered ring pore structure and a Si/Me-ratio higher than 39, preferably higher than 77.5.

12. Process according to claim 2, wherein the microporous zeolite material comprises, inside its pores, a hydrogenation metal catalyst selected from the group consisting of platinum, palladium, nickel, copper, cobalt, rhodium, ruthenium and mixtures thereof.

13. Process according to claim 3, wherein the microporous zeolite material comprises, inside its pores, a hydrogenation metal catalyst selected from the group consisting of platinum, palladium, nickel, copper, cobalt, rhodium, ruthenium and mixtures thereof.

* * * * *